United States Patent [19]
Davis

[11] Patent Number: 5,562,652
[45] Date of Patent: Oct. 8, 1996

[54] ANTISEPTIC MEDICAL APPARATUS

[76] Inventor: William M. Davis, 12333 E. Calle del Gorrion, Tucson, Ariz. 85748

[21] Appl. No.: 319,971

[22] Filed: Oct. 7, 1994

[51] Int. Cl.$^6$ ........................................ A61K 9/22
[52] U.S. Cl. ........................ 604/890.1; 604/19; 604/96; 604/264
[58] Field of Search .................. 604/11, 96, 53, 604/97, 98, 99, 100, 101, 102, 103, 19, 890.1, 264, 349; 602/48

[56] References Cited

U.S. PATENT DOCUMENTS

| | | |
|---|---|---|
| 3,894,540 | 7/1975 | Bonner, Jr. . |
| 4,343,788 | 8/1982 | Mustacich et al. . |
| 4,479,795 | 10/1984 | Mustacich et al. . |
| 4,620,527 | 11/1986 | Adams, Jr. . |
| 4,685,455 | 8/1987 | Vrouenraets . |
| 5,098,379 | 3/1992 | Conway et al. . |
| 5,137,671 | 8/1992 | Conway et al. . |
| 5,176,665 | 1/1993 | Watanabe et al. .............. 604/317 |
| 5,176,666 | 1/1993 | Conway et al. . |
| 5,185,007 | 2/1993 | Middaugh et al. .............. 604/319 |
| 5,236,422 | 8/1993 | Eplett, Jr. . |
| 5,261,896 | 11/1993 | Conway et al. . |
| 5,269,755 | 12/1993 | Bodicky . |
| 5,269,770 | 12/1993 | Conway et al. . |
| 5,334,175 | 8/1994 | Conway et al. . |

Primary Examiner—Corrine M. McDermott
Assistant Examiner—N. Kent Gring
Attorney, Agent, or Firm—Austin R. Miller

[57] ABSTRACT

A water activated antiseptic sheet including a base member having opposed surfaces and a reservoir located within the base member, the reservoir containing a water-activated antiseptic agent, wherein at least a portion of the base member between at least one of the opposed surfaces and the reservoir permit permeation of water vapor toward and into the reservoir and diffusion of antiseptic compound formed from the water activated antiseptic agent toward at least one of the opposed surfaces.

24 Claims, 3 Drawing Sheets

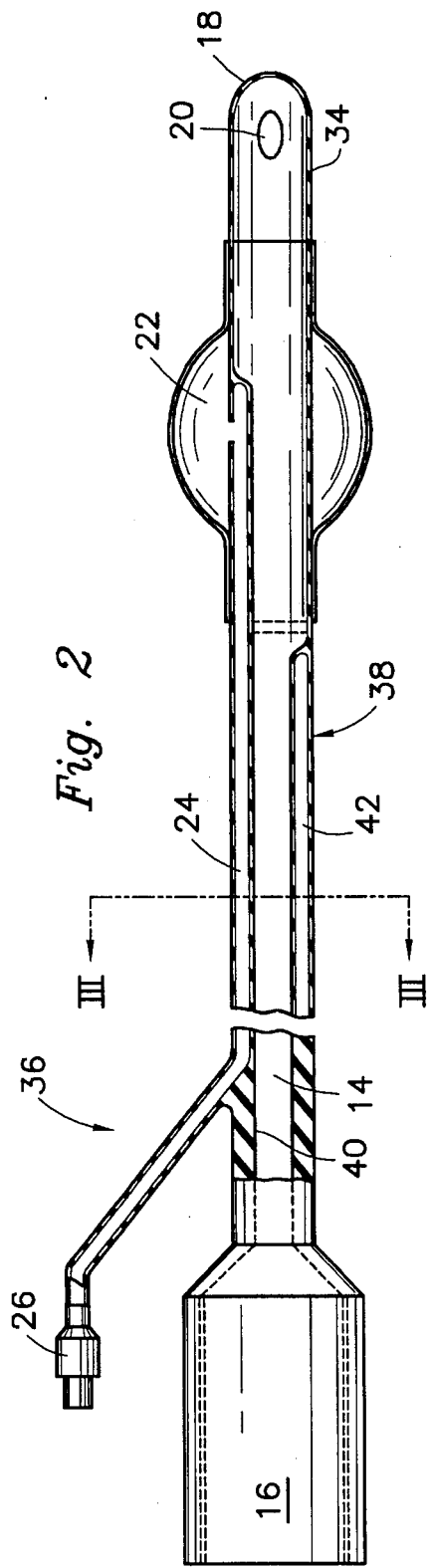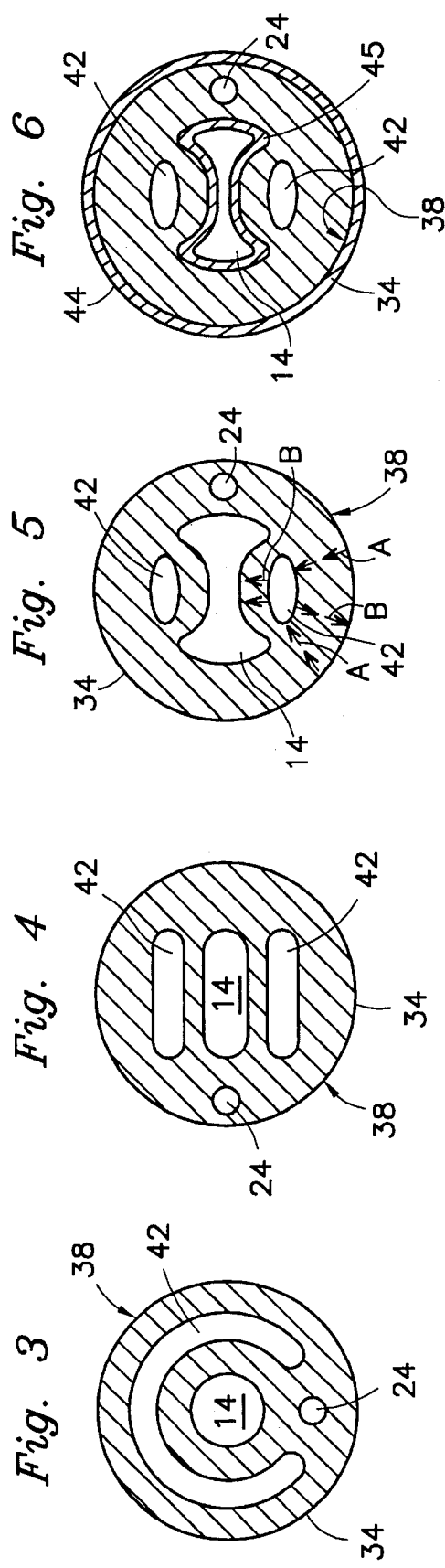

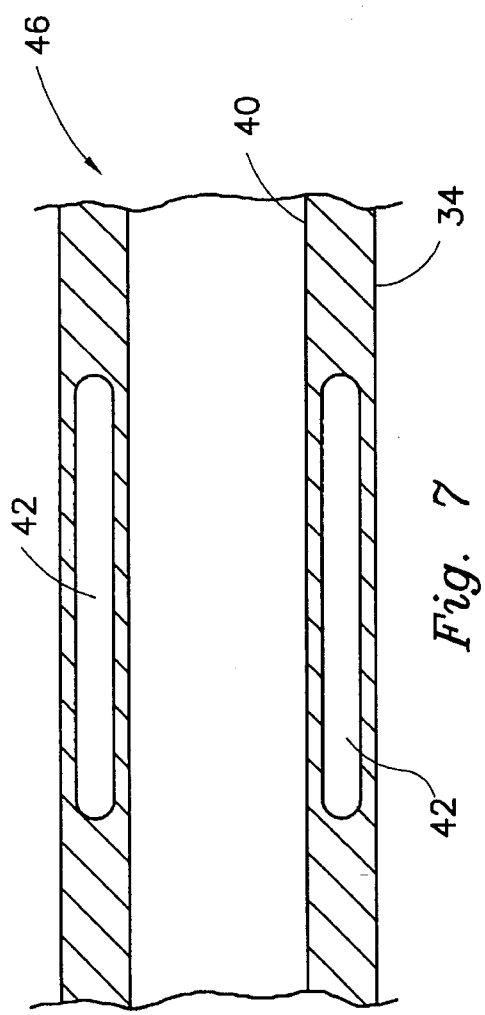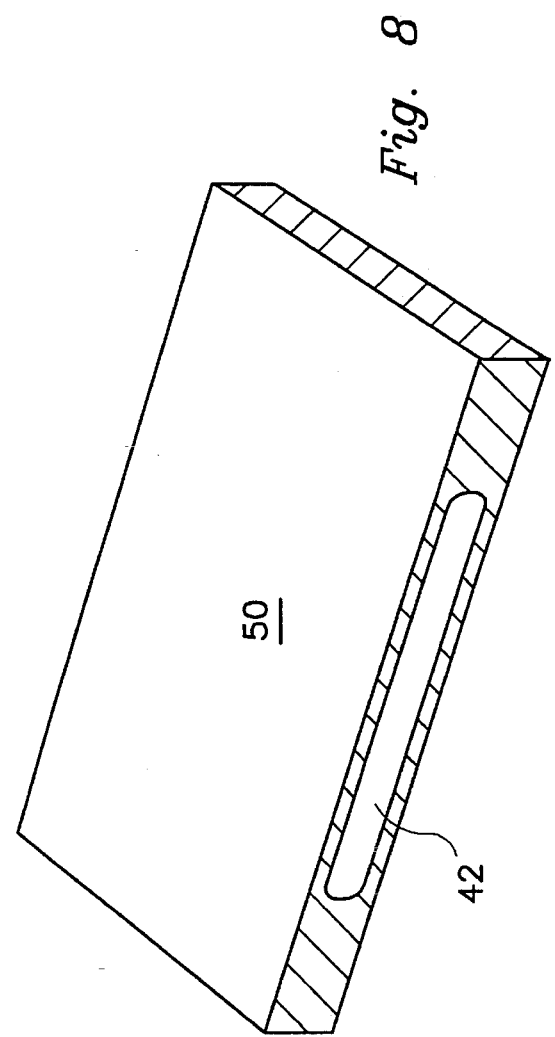

ANTISEPTIC MEDICAL APPARATUS

FIELD OF THE INVENTION

The present invention relates to medical devices having antiseptic capabilities, particularly to a urinary catheter capable of extended indwelling duration having excellent antiseptic capabilities.

BACKGROUND OF THE INVENTION

In the practice of human and veterinary medicine, it is often desirable and necessary to use various polymeric devices such as urinary catheters, cerebro peritoneal shunts, breast implants, artificial joints, hemodialysis devices and the like to treat or diagnose disease. Such devices are often contaminated by bacteria, fungus, viruses and other organisms or infective proteins, resulting in systemic and/or local infection. Such contaminants sometimes lead to sepsis and death. This phenomenon is further aggravated by contact of the device, such as urinary tract Foley type catheters, for example, by external mammalian tissues, such as skin or mucous membranes which themselves are carriers of potentially infective organisms.

Various proposals have been made in the past to provide protection for such devices such as catheters and various bacteriostats and bactericides have been applied to the surfaces of urinary catheters to prevent infection. However, none of these have been completely effective and the danger of infection and the potentially fatal problems it presents is always present, particularly in the case of indwelling catheters such as urinary tract Foley type catheters.

It has also been believed that therapeutic risk involved with the use of medical devices could be controlled, eliminated or attenuated if the device itself had antiseptic properties. Medical use and research has demonstrated that antibiotic use alone such as systemic treatment separate from local application to the device, is ineffective for long term antisepsis due to bacterial resistance and sometimes drug allergic reaction. Therefore, the use of an antiseptic agent whose anti-infective organism-effects are multi focal and wide-spectra is necessary if long term and safe antisepsis is to be imported to the device. It has become readily apparent that many agents, while not developing microorganism resistance, have a limited spectrum such as nitrofurazone and chloroxylenol, which are weakly effective against Pseudomonas and some Proteus, silver sulfadiazine, which is weakly effective against *Staphylococcus aureus* and Pseudomonas, and mandelic acid, which is weakly effective against Proteus. It has accordingly not been possible to achieve reliable long term indwelling of urinary catheters capable of effective antiseptic action.

This problem has been especially prevalent in urinary retention catheters such as Foley catheters. Retention catheters connect the patient's bladder to the meatus of the patient to continuously remove urine from the patient's bladder. Sources of urinary retention catheter related urinary tract infections are suspected to be bacteria progressing from the patient's meatus through the peri-urethral space into the bladder or the catheter lumen. A number of methods and devices in the prior art for attempting to prevent bacterial caused urinary tract infections are disclosed. Examples include U.S. Pat. Nos. 4,773,901; 5,098,379; 5,236,422; 5,261,896; 5,269,755 and 5,269,770. However, for many applications, these devices have not proved to be totally effective. As a result, a substantial probability of acquiring a urinary tract infection still exists when using these devices.

OBJECTS OF THE INVENTION

It is an object of the present invention to provide medical apparatus such as a catheter having self contained antiseptic properties and capable of preventing infection against a wide variety of microorganisms.

It is another object of the invention to provide a urinary catheter capable of extended periods of release of antiseptic compound, especially for preventing urinary tract infections.

It is still another object of the invention to provide a means for preventing infection in a variety of devices such as shunts, stents, catheters, cannulas, implants, tubes, bags, sheets and the like that are contacted with tissue.

Other objects and advantages of the invention will become apparent to those skilled in the art from the drawings, the detailed description of detailed embodiments and the appended claims.

SUMMARY OF THE INVENTION

The present invention provides apparatus for preventing infection caused by devices used to treat or diagnose disease or ailments. The invention particularly relates to a urinary catheter having antiseptic capabilities that is adapted for extended retention periods. The catheter is preferably a Foley-type catheter and includes a elongated conduit having inner and outer surfaces with the inner surface defining a lumen passing along the catheter to transport urine. A reservoir is located within the conduit and along the catheter, the reservoir containing a water-activated antiseptic agent. At least a portion of the conduit located between the inner and/or outer surfaces and the reservoir is formed from a material adapted to permit inward permeation of water toward the reservoir and diffusion of an antiseptic compound formed as a reaction product of the water-activated antiseptic compound toward the surfaces of the device or catheter. Preferably, the elongated conduit is formed entirely from the permeable material. The water-activated antiseptic compound is preferably a halophor.

BRIEF DESCRIPTION OF THE DRAWINGS

FIG. 2 shows a front elevational view, partly taken in section, of a catheter of the invention.

FIG. 3 is a cross-sectional view of the catheter shown in FIG. 2 at the lines and arrows III—III.

FIG. 4 is a cross-sectional view similar to that shown in FIG. 3 of another embodiment of the invention.

FIG. 5 is a cross-sectional view of another embodiment of a catheter similar to that depicted in FIGS. 3 and 4.

FIG. 6 is a cross-sectional view of a catheter in accordance with embodiments of the invention and including a diffusion barrier formed thereon.

FIG. 7 is a front elevational view, taken in section, of a portion of a tube having antiseptic capabilities in accordance with the invention and adapted for use in medical apparatus such as catheters, cannulas, shunts, stents, joints, implants and the like.

FIG. 8 is a perspective view of a portion of a sheet having antiseptic capabilities in accordance with the invention.

DETAILED DESCRIPTION OF THE INVENTION

Figure 1:
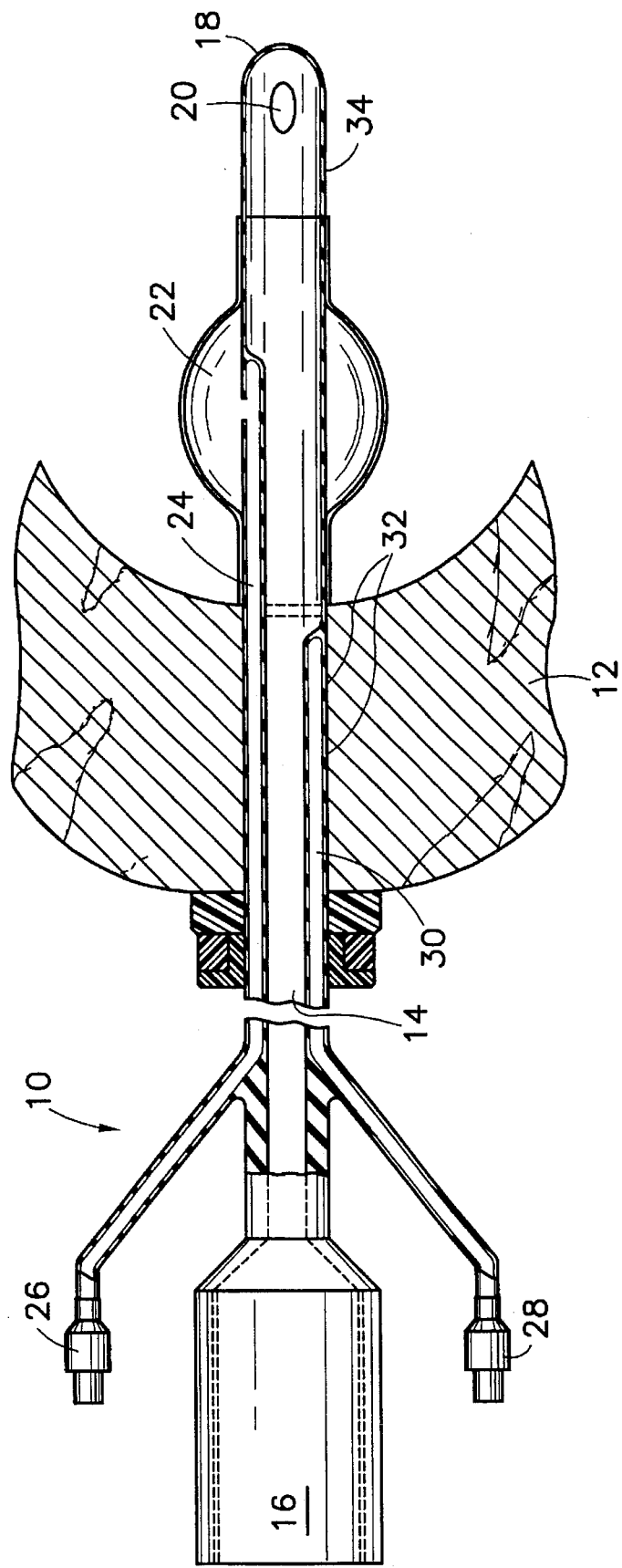
FIG. 1 shows a front elevational view, taken partly in section, of a prior art Foley-type catheter extending into a bladder.

It will be appreciated that the following description is intended to refer to the specific embodiments of the invention selected for illustration in the drawings and is not intended to define or limit the invention other than in the appended claims.

Turning now to the drawings in general, and FIG. 1 in particular, the number 10 designates a Foley-type catheter retained in a desired position relative to bladder 12. Catheter 10 includes a central lumen 14 which terminates at its proximal end in a coupling 16 and a curved tip 18 on its distal end. Tip 18 includes hole 20 for ingress of urine. Urine entering hole 20 passes along central tube 14 and outwardly of catheter 10 by way of coupling 16. The distal end also includes an inflatable balloon 22 which assists in retaining catheter 10 in position. Balloon 22 is inflated and deflated by causing inflation fluid to flow through inflation passageway 24 which connects to inflation portal 26. A medicament portal 28 connects to the proximal end of catheter 10 and is contiguous with medicament passageway 30 in catheter 10. A plurality of medicament holes 32 extend through outer surface 34 of catheter 10 and into contact with the surrounding tissue of bladder 12. Medicaments, lubricants and the like are applied to the surrounding tissue by introduction into medicament portal 28, through medicament passageway 30 and outwardly through medicament holes 32.

Although catheters of the type shown in FIG. 1, including their means for applying medicament directly to nearby tissue, are improved over prior catheters, they still retain several disadvantages such as the need for complicated and cumbersome structure. Such structure includes medicament portal 28, medicament passageway 30 and medicament holes 32, for example. From an operational standpoint, it is also necessary to repeatedly or continuously supply medicament to the affected area during the entire retention time of the catheter 10 within bladder 12. This requires constant monitoring and increased attention by attending staff. There is also a possible problem associated with inadequate application of medicament in the event that one or more of the medicament holes become plugged or there is a "short circuit." These and other problems have now been solved by the invention as described below and illustrated in the drawings.

FIG. 2 depicts one embodiment of a catheter 36 of the invention. Catheter 36 includes a tubular member 38 which connects on its proximal end to a coupling 16 and terminates at its distal end in a closed tip 18. Closed tip 18 contains hole 20 which permits ingress of urine into central lumen 14 for passage outwardly via coupling 16. Tubular member 38 has an outer surface 34 which contacts surrounding tissue and an inner surface 40 which forms central lumen 14. Catheter 36 also includes an inflation portal 26 connected to inflation passageway 24. Inflation passageway 24 connects to balloon 22 in the usual manner.

However, in a sharp departure from other devices, catheter 36 is provided with a closed reservoir 42 which contains a water-activated antiseptic agent. The water-activated antiseptic agent is inactive in reservoir 42 prior to use and is "activated" only upon contact with water or water vapor. Upon contact, water vapor and water-activated antiseptic agent chemically react and form reaction products which have antiseptic capabilities, hereinafter referred to as "antiseptic compounds." Reservoir 42 may be sized to fit the particular need, although a volume of 2000 mm$^3$ for an 18 French size Foley catheter is especially preferred.

The preferred water activated antiseptic agent is a halophor. Preferred halophors include iodophors and chlorophors. A particularly preferred iodophor is povidone iodine. The most preferred chlorophors include oxychlorosene, trichloroisocyanuric acid and N-chloro-succinimide. The chlorophors also include N-chloro substituted amines, amides and other imides. Hypochlorite solutions and chlorinated lime also constitute chlorophors that may be used in the invention. When the iodophor povidone iodine is employed in reservoir 42, reaction with water vapor produces iodine and/or hypoiodous acid, both of which have antiseptic capabilities and are antiseptic compounds. Similarly, trichloroisocyanuric acid produces hypochlorous acid and/or chlorine as antiseptic compounds upon reaction with water vapor.

The halophors may be supplied to reservoir 42 in varying concentrations, preferably at concentrations of about 10–40%, most preferably about 20%, for a trichloroisocyanuric acid halophor and about 20–60%, most preferably about 30%, for an N-chloro-succinimide halophor.

At least a portion of tubular member 38 located between outer surface 34 and reservoir 42 is constructed from a material which permits diffusion of water vapor from surrounding tissue inwardly toward and into reservoir 42 triggering the production of antiseptic moities produced from the water-activated antiseptic agent and also the production of carrier molecules, which cannot penetrate through the outer surface 34. Examples of such carrier molecules are polyvinyl pyrrolidone in the case of povidone iodine and cyanuric acid in the case of trichloroisocyanuric acid. In a preferred form, at least a portion of tubular member 38 located between inner surface 40 and reservoir 42 is constructed from the material to permit diffusion of antiseptic compounds produced from the water-activated antiseptic agent toward inner surface 40 and lumen 14. In its most preferred form, tubular member 38 is constructed entirely from the same material. An especially preferred material is elastomeric silicones such as silicone rubber. Other materials such as fluorohydrocarbons may be employed. It is especially preferred that polymeric materials selected for tubular member 38 be vulcanized polymeric materials.

FIG. 3 shows a cross section of the catheter shown in FIG. 2 wherein tubular member 38 contains inflation passageway 24 and reservoir 42. Reservoir 42 is located just below, but adjacent to outer surface 34 of tubular member 38.

FIG. 4 shows another embodiment of tubular member 38 of catheter 36 wherein reservoir 42 is located at a position closer to lumen 14, at a distance further removed from outer surface 34.

FIG. 5 shows still another embodiment of catheter 36 wherein lumen 14 is not centrally located along the center axis of catheter 36 and reservoir 42 is located still further away from outer surface 34. Arrows "A" represent a diffusion path for water vapor to migrate inwardly toward reservoir 42. Arrows "B" represent a diffusion path for antiseptic compound to migrate inwardly and outwardly from reservoir 42.

Variations in the structure of catheter 36 as shown in FIGS. 3–5, permit variations in the antiseptic activity of the antiseptic compound. For example, the embodiment shown in FIG. 3 permits comparatively rapid diffusion of antiseptic compound outwardly of catheter 36 relative to the diffusion rate of antiseptic compound in the embodiment shown in FIGS. 4 and 5. Structural alterations such as those depicted in FIGS. 3–5 can be employed to meet a variety of conditions such as the desired retention time of catheter 36, the type of antiseptic compound, the concentration of the antiseptic compound, the type of microorganisms likely to be encountered, the type of surrounding tissue and the like.

An alternative structure is shown in FIG. 6 wherein a diffusion barrier 44 is concentrically positioned outwardly of tubular member 38 on outer surface 34 and a diffusion barrier 45 is inwardly positioned on inner surface 40 along lumen 14. The diffusion barrier can be selected from a wide variety of materials, so long as they permit diffusion of water vapor and the antiseptic compounds, to further control the diffusion rate of antiseptic agents outwardly from catheter 36. Especially preferred among the materials for the diffusion barrier are fluorinated polymeric hydrocarbons. Those materials provide the added advantage of low coefficients of friction which assists in insertion and movement of the catheter against and along sensitive surrounding tissues.

In use, catheter 36 is applied to the appropriate passageway, such as the urinary tract, in the usual manner for the particular task. However, the amount, type and concentration of the water activated antiseptic agent in reservoir 42 is pre-determined and pre-contained prior to insertion, thereby avoiding a wide variety of the problems of prior art devices. The water-activatable antiseptic agent contained within reservoir 42 is inactive prior to insertion and is only activated upon diffusion of water vapor through tubular member 38 and into contact with the water activated antiseptic agent in reservoir 42. Water from the surrounding tissues diffuses as water vapor through tubular member 38 in the manner indicated by arrows "A" in FIG. 5 and into reservoir 42. The chemical reaction between the water vapor and water activated antiseptic agent proceeds within reservoir 42 by virtue of the diffusion that occurs over the course of time, depending on factors such as the particular water-activated antibacterial agent, its concentration within reservoir 42, the distance between reservoir 42 and outer surface 34 or lumen 14, the presence or absence of a diffusion barrier, the amount of water vapor supplied from the surrounding tissues, the water permeability of the material selected for tubular member 38 and the like. Antiseptic compound then diffuses inwardly and/or outwardly as shown by arrows "B" in FIG. 5 toward outer surface 34 and lumen 14. By knowing and preselecting combinations of these variables, catheter 36 reliably applies antiseptic compounds to the affected tissues or into lumen 14 in a manner that reliably prevents infection and provides for increased retention times beyond those contemplated in the art.

FIG. 7 shows a portion of a tube 46 that may be used as or in conjunction with a variety of medical devices. Such devices include catheters, shunts, stents, joints, implants, bags, cannulas and the like. Tube 46 includes a pair of reservoirs 42 located opposite one another and between outer surface 34 and inner surface 40. Each reservoir 42 contains water activatable antiseptic agent in the same manner as shown in FIGS. 2–6. Tube 46 may be flattened into a sheet or plate if desired by performing a longitudinal cut. Alternatively, a sheet or plate 50 may be directly formed, such as shown in FIG. 8, the thickness of which may be varied as needed to suit the task. The sheet or plate has a reservoir 42 and may have varying degrees of stiffness as desired. Tube 46 and sheet 50 may also have diffusion barriers applied to one or both of their surfaces as desired.

Although this invention has been described in connection with specific forms thereof, it will be appreciated that a wide variety of equivalents may be substituted for the specific elements shown and described herein without departing from the spirit and scope of this invention as described in appended claims.

For example, catheters of the invention may have a wide variety of structures, materials and shapes, all known in the art. Also, the catheters of the invention are not limited to use as urinary catheters, but may be employed in a wide variety of uses in a wide variety of mammals and in passageways wherever antiseptic/antibacterial/antimicrobial capabilities are required. The number of reservoirs 42 may be adjusted as desired. For example, multiple reservoirs 42 may be arranged in an end-to-end configuration, multiple reservoirs may be provided in a selected cross-section, an entire cross-section may be one reservoir, in which case the water activated agent may be finely divided and interspersed throughout tubular member 38 having been introduced by coextrusion, and the like. Similarly, the shape and orientation of reservoirs 42 may be selected as desired.

The construction of tubular member 38 may be selected from a variety of configurations. For example, inner surface 40 and outer surface 34 need not be concentric relative to teach other and need not be similarly shaped. Shapes of all types, including but not limited to circular, square, oval, rectangular, triangular and the like are all contemplated.

Tubular member 38 may also be constructed of a multiplicity of layers to perform various tasks as desired. For example, multiple layers having different strengths, fluid resistivities, and the like may be employed, so long as the water vapor and antiseptic compound diffusion characteristics adjacent reservoir 42 are retained. Moreover, it is possible to use any number of methods for forming tubular member 38 known in the art. Particularly preferred methods include extrusion and coextrusion methods known in the art. Coextrusion such as that disclosed in U.S. Pat. No. 4,533,510 is one example.

What is claimed is:

1. A water vapor activatible antiseptic sheet comprising:

a base member having opposed surfaces; and a reservoir located within said base member, said reservoir containing a water vapor-activatible antiseptic agent, wherein at least a portion of said base member between at least one of said opposed surfaces and said reservoir is constructed from a selectively permeable material which diffuses water vapor toward and into said reservoir for reaction with said antiseptic agent therein and diffuses antiseptic reaction product formed from said water vapor activatible antiseptic agent out of said reservoir for patient treatment.

2. The sheet defined in claim 1 wherein said sheet is extruded.

3. The sheet defined in claim 1 wherein said reservoir retains molecules of said water activated antiseptic agent while releasing said antiseptic compound.

4. A water activated antiseptic tube comprising:

an elongated conduit having an inner surface and an outer surface, said inner surface defining a passageway passing through at least a portion of said tube, and a reservoir located within said conduit along at least a portion of said tube, said reservoir containing a water-activated antiseptic agent, wherein at least a portion of said conduit is formed from a material which permits water vapor permeation through said portion and into said reservoir and diffusion of antiseptic compound formed from said water activated antiseptic agent toward said inner and/or outer surfaces.

5. The tube defined in claim 4 adapted for use in a medical device selected from the group consisting of shunts, stents, cannulas, implants, joints and catheters.

6. The tube defined in claim 4 wherein said reservoir retains molecules of said water activated antiseptic agent while releasing said antiseptic compound.

7. A catheter comprising:

an elongated conduit having an inner surface and an outer surface, said inner surface defining a lumen passing through at least a portion of said catheter, and a reservoir located within said conduit along at least a portion of said catheter, said reservoir containing a water-activated antiseptic agent, wherein at least a portion of said conduit is formed from a material which permits water vapor permeation through said portion and into said reservoir and diffusion of antiseptic compound formed from said water activated antiseptic agent toward said inner and/or outer surfaces.

8. The catheter defined in claim 7, wherein said water-activated antiseptic agent is a halophor.

9. The catheter defined in claim 7, wherein said water-activated antiseptic agent is an iodophor or a chlorophor.

10. The catheter defined in claim 7, wherein said water-activated antiseptic agent is selected from the group consisting of oxychlorosene, trichlorisocyanuric acid, N-chlorosuccinimide and povidone iodine.

11. The catheter defined in claim 7, wherein said reservoir contains only said water-activated antiseptic agent.

12. The catheter defined in claim 7, wherein said reservoir is free of carrier liquids and/or lubricants.

13. The catheter defined in claim 7, wherein said material is silicone rubber.

14. The catheter defined in claim 7, wherein said material is vulcanized.

15. The catheter defined in claim 7, wherein said conduit is entirely formed from said material.

16. The catheter defined in claim 7, wherein said material permits inward permeation of water vapor.

17. The catheter defined in claim 7, wherein said material permits inward and outward diffusion of said antiseptic compound formed as a reaction product of said water-activated antiseptic compound and water vapor.

18. The catheter defined in claim 7, further comprising a diffusion barrier formed on at least a portion of said inner and/or outer surfaces.

19. The catheter defined in claim 18, wherein said diffusion barrier is a fluorinated polymeric hydrocarbon.

20. The catheter defined in claim 7, further comprising an inflatable balloon located on said conduit and a passageway located in said conduit and adapted to inflate and deflate said balloon.

21. The catheter defined in claim 7, wherein said catheter is a Foley catheter.

22. A catheter for insertion into a passageway in a mammal comprising:

an elongated tubular member having an inner wall and an outer wall, at least a portion of said tubular member being formed from a material permitting permeation of water vapor through said outer wall, and a chamber located inwardly of said outer wall containing a water-activated agent which reacts with water vapor and form an antiseptic compound as a product, said chamber positioned adjacent said material to receive water vapor permeating from said outer wall and to diffuse said antiseptic compound outwardly and/or inwardly.

23. The catheter defined in claim 22, wherein said catheter is a urinary catheter.

24. Antiseptic medical apparatus comprising:

a base member having opposed surfaces; and a reservoir located within said base member, said reservoir containing a tissue temperature water vapor activatible antiseptic agent, wherein at least a portion of said base member between at least one of said opposed surfaces and said reservoir is constructed from a selectively permeable material which diffuses water vapor at tissue temperature toward and into said reservoir for reaction with said antiseptic agent therein and diffuses antiseptic reaction product formed from said tissue temperature water vapor activatible antiseptic agent out of said reservoir for patient treatment.

* * * * *